(12) United States Patent
Chung

(10) Patent No.: US 8,146,608 B2
(45) Date of Patent: Apr. 3, 2012

(54) DENTAL FLOSS HOLDING STRUCTURE

(75) Inventor: Wu-Chang Chung, Taipei (TW)

(73) Assignee: Kin Denfra Co., Ltd., Taipei (TW)

( * ) Notice: Subject to any disclaimer, the term of this patent is extended or adjusted under 35 U.S.C. 154(b) by 171 days.

(21) Appl. No.: 12/648,734

(22) Filed: Dec. 29, 2009

(65) Prior Publication Data

US 2011/0155168 A1    Jun. 30, 2011

(51) Int. Cl.
*A61C 15/00*    (2006.01)
(52) U.S. Cl. ........................................................ 132/323
(58) Field of Classification Search .................. 132/321, 132/323, 326–328
See application file for complete search history.

(56) References Cited

U.S. PATENT DOCUMENTS

| 4,016,892 A | 4/1977 | Chodorow |
| 7,464,716 B1 * | 12/2008 | Nygren, Jr. .................. 132/322 |

* cited by examiner

*Primary Examiner* — Rachel Steitz
(74) *Attorney, Agent, or Firm* — Muncy, Geissler, Olds & Lowe, PLLC

(57) ABSTRACT

A dental floss holding structure includes a dental floss and two holding bodies. The two ends of the dental floss are respectively connected with a base, which includes a first coupling portion with a first positioning portion mounted thereon. Each of the two holding bodies includes a second coupling portion corresponding to the first coupling portion, and the second coupling portion has a second positioning portion corresponding to the first positioning portion, so that the dental floss and the holding bodies can be stably fixed with each other through the engagement between the first and the second positioning portions. Accordingly, when the user's hands hold the two holding bodies to clean the teeth slits, the fingers can be kept out of the mouth without entering the mouth, which not only provides convenience but also assures the hygiene.

5 Claims, 4 Drawing Sheets

DENTAL FLOSS HOLDING STRUCTURE

FIELD OF THE INVENTION

The present invention is related to a dental floss holding structure, and more particularly to a holding structure for a dental floss used to clean the slits between the teeth.

BACKGROUND OF THE INVENTION

It is very important to keep the mouth cavity clean, especially the cleanness of the teeth. Most people brush their teeth after waking up or before going to bed. However, the time the teeth erosion mostly happens is after a meal because the acid concentration within the mouth is constantly increased, and if the teeth do not be cleaned right after the meal, the teeth might easily become damaged. Although brushing the teeth is one of the commonest ways to keep the teeth clean, it only can clean the surfaces of the teeth and has difficulty in cleaning the slits between the teeth. Therefore, the cleanness of the teeth slits becomes more important.

The traditional way for cleaning the teeth slits is to use a toothpick. However, since the toothpick is made of a relatively harder material and also has a larger diameter, it might widen the teeth slits after a long-term usage, and the widened teeth slits not only look not beautiful, but also might easily have the food residues stuck therein. Therefore, the dentist now recommends using the dental floss to clean the teeth slits. U.S. Pat. No. 4,016,892 disclosed that a holding piece is respectively mounted at the two ends of a dental floss for being held by the user to clean the teeth slits, thereby achieving a more efficient cleaning operation. And, this architecture is also benefit for manufacture. The holding pieces can be mounted on a bundle of dental floss at a preset distance so as the dental floss can be separated into multiple singly used lengths. This not only provides the user the basis to cut off the dental floss, but also reaches the purpose of mass production.

However, the above patent still has some disadvantages:

1. The length of the holding piece is so short that the user's fingers have to go deep into the mouth for cleaning the teeth slits, and since the fingers are easily contaminated by dirt and bacteria, it is easy to transfer the dirt and bacteria into the mouth as using the dental floss, so as to endanger the oral hygiene.

2. The fingers will need to pull and drag with this short dental floss inside the mouth, and for users with thick fingers, the operation difficulty might be further increased.

SUMMARY OF THE INVENTION

The object of the present invention is to solve the problems described above, so as to prevent the fingers from entering the mouth as using the dental floss to clean the teeth slits.

For achieving the object described above, the present invention provides a dental floss holding structure including a dental floss and two holding bodies. The two ends of the dental floss are respectively connected with a base, which includes a first coupling portion with a first positioning portion mounted thereon. Each of the two holding bodies includes a second coupling portion corresponding to the first coupling portion; and the second coupling portion has a second positioning portion corresponding to the first positioning portion, so that the dental floss and the holding bodies can be stably fixed with each other through the engagement between the first and the second positioning portions.

Accordingly, as compared with the conventional techniques, the present invention is advantageous that:

1. As operating, by using the holding bodies, the user's fingers can be kept out of the mouth, thereby avoiding the entrance of the fingers into the mouth, and thus, preventing from the invasion of the dirt and bacteria, so as to maintain the oral hygiene.

2. The diameter of the holding body is relatively smaller than that of the fingers, so that the operation space in the mouth is relatively larger, which provides more convenient and simpler operation procedure.

3. After using, the dental floss together with the bases can be detached from the holding bodies, so that not only the second coupling portions of the holding bodies can be cleaned for further assuring the hygiene of the mouth, but also the holding bodies can be reused to achieve the environmental protection.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DESCRIPTION OF THE PREFERRED EMBODIMENT

Figure 1:
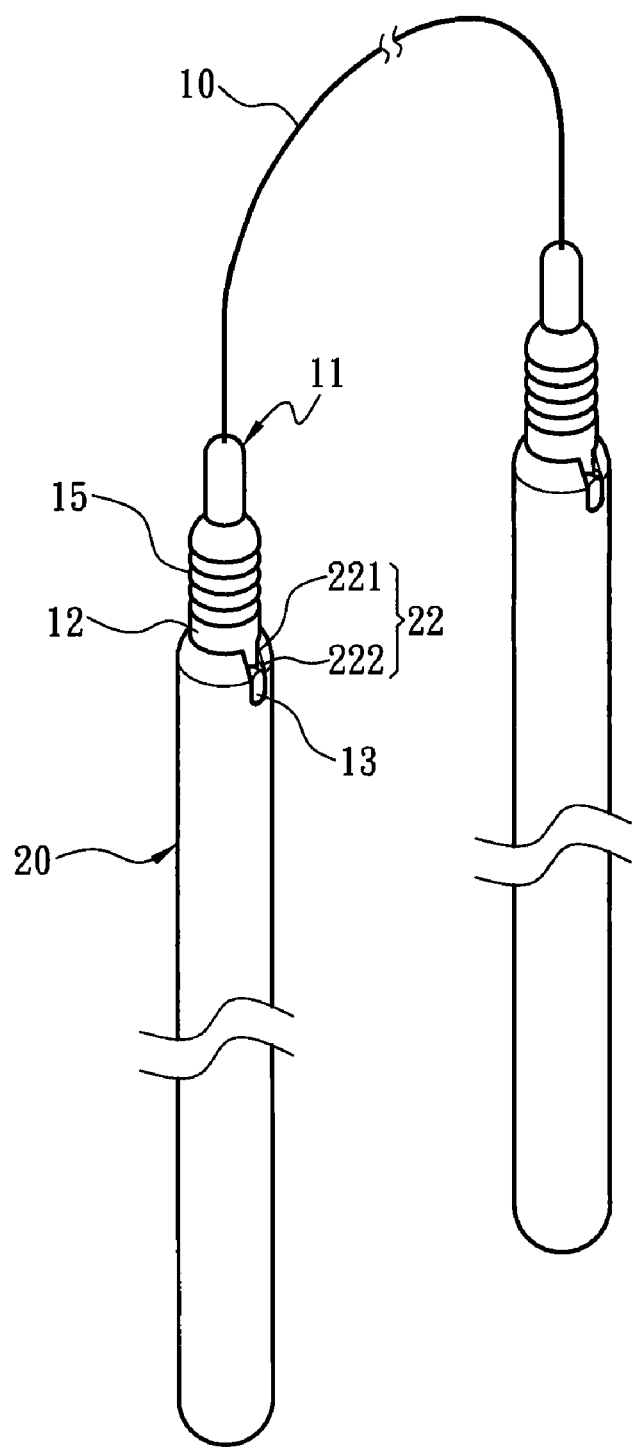
FIG. 1 is a schematic view showing the present invention.

Please refer to FIG. 1. The present invention is related to a dental floss holding structure, including a dental floss 10 and two holding bodies 20, wherein a base 11 is respectively mounted on two ends of the dental floss 10, and the two holding bodies 20 are respectively connected with the bases 11, and thus located at the two ends of the dental floss 10.

Figure 2:
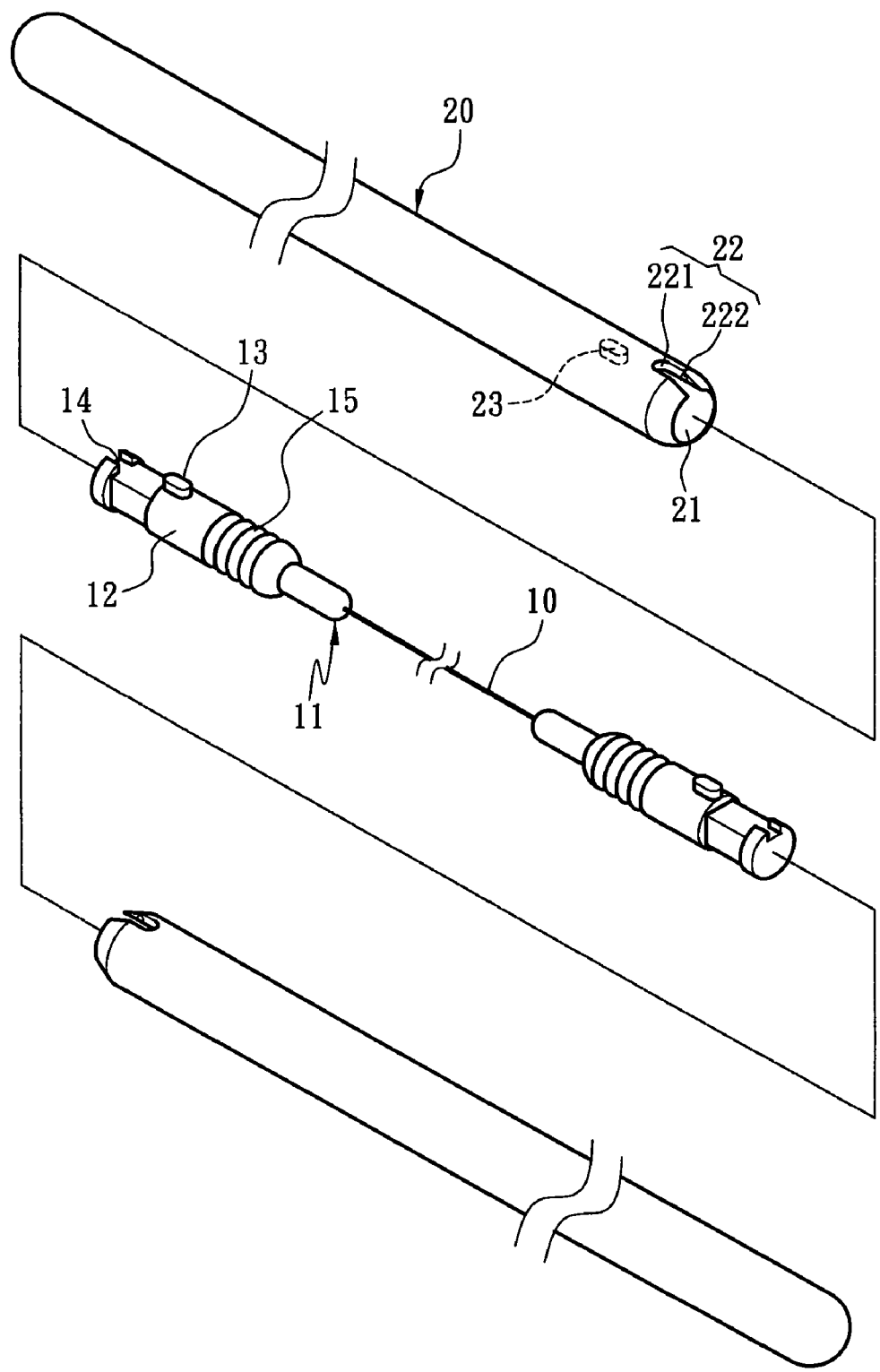
FIG. 2 is an exploded view showing the present invention.
Figure 3:
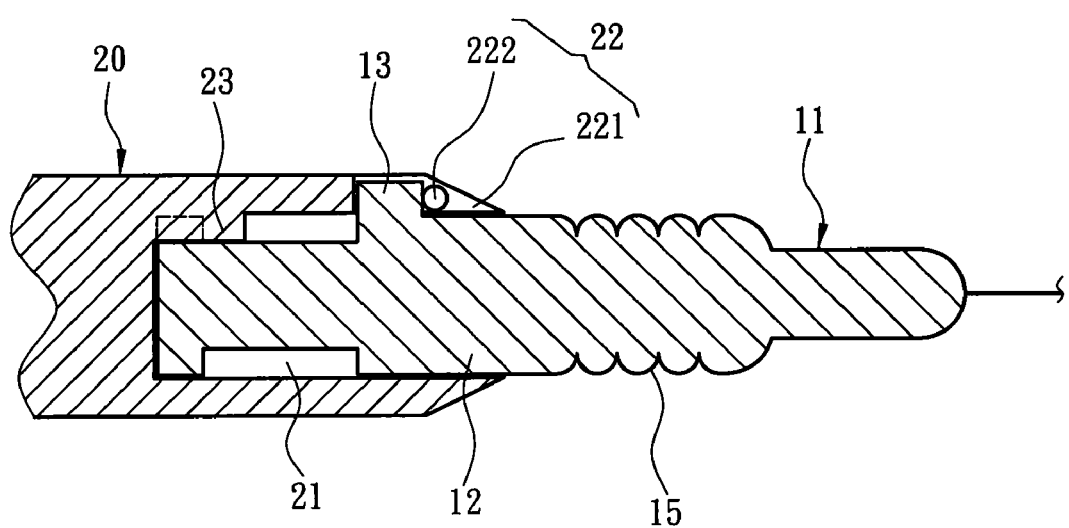
FIG. 3 is a fragmentary sectional view showing the present invention.

Please further refer to FIG. 2 and FIG. 3. The base 11 and the holding body 20 respectively have a first coupling portion 12 and a second coupling portion 21. In this embodiment, the first coupling portion 12 is a column and the second coupling portion 21 is a notch for receiving the column of the first coupling portion 12, so as to form a male-female structure. Furthermore, the first coupling portion 12 and the second coupling portion 21 respectively have a first positioning portion 13 and a second positioning portion 22, which are corresponding to each other, so that the dental floss 10 and the holding body 20 can form a stable fixed relationship through the engagement between the first and the second positioning portions 13, 22. Here, the first positioning portion 13 is a protrusion and the second positioning portion 22 is an indentation 221 for receiving the protrusion. Moreover, the indentation 221 of the second positioning portion 22 further has a locking block 222 mounted thereon, so that when the first coupling portion 12 of the base 11 is inserted into the second coupling portion 21 of the holding body 20, the protrusion of the first positioning portion 13 is inserted into the indentation 221 of the second positioning portion 22 and further engaged with the locking block 222 of the second positioning portion 22 to form a stable fixed relationship. Therefore, the dental floss 10 can be stably fixed on the holding body 20, and at the same time, a rotation between the first coupling portion 12 and the second coupling portion 21 also can be avoided. In addition, the first coupling portion 12 and the second coupling portion 21 respectively further form a first position-limiting portion 14 and a second position-limiting portion 23, which can be mutually engaged for achieving the purpose of position-limiting. Here, the first position-limiting portion 14 is an indentation and the second position-limiting portion 23 is a bulge corresponding thereto, so as to stably assemble the first coupling portion 12 with the second coupling portion 21, and thus prevent the rotation therebetween. Besides, the bases 11 are also provided with rough lines 15 mounted on the surface thereof for facilitating the holding by the user and connecting with the holding bodies 20.

Figure 4:
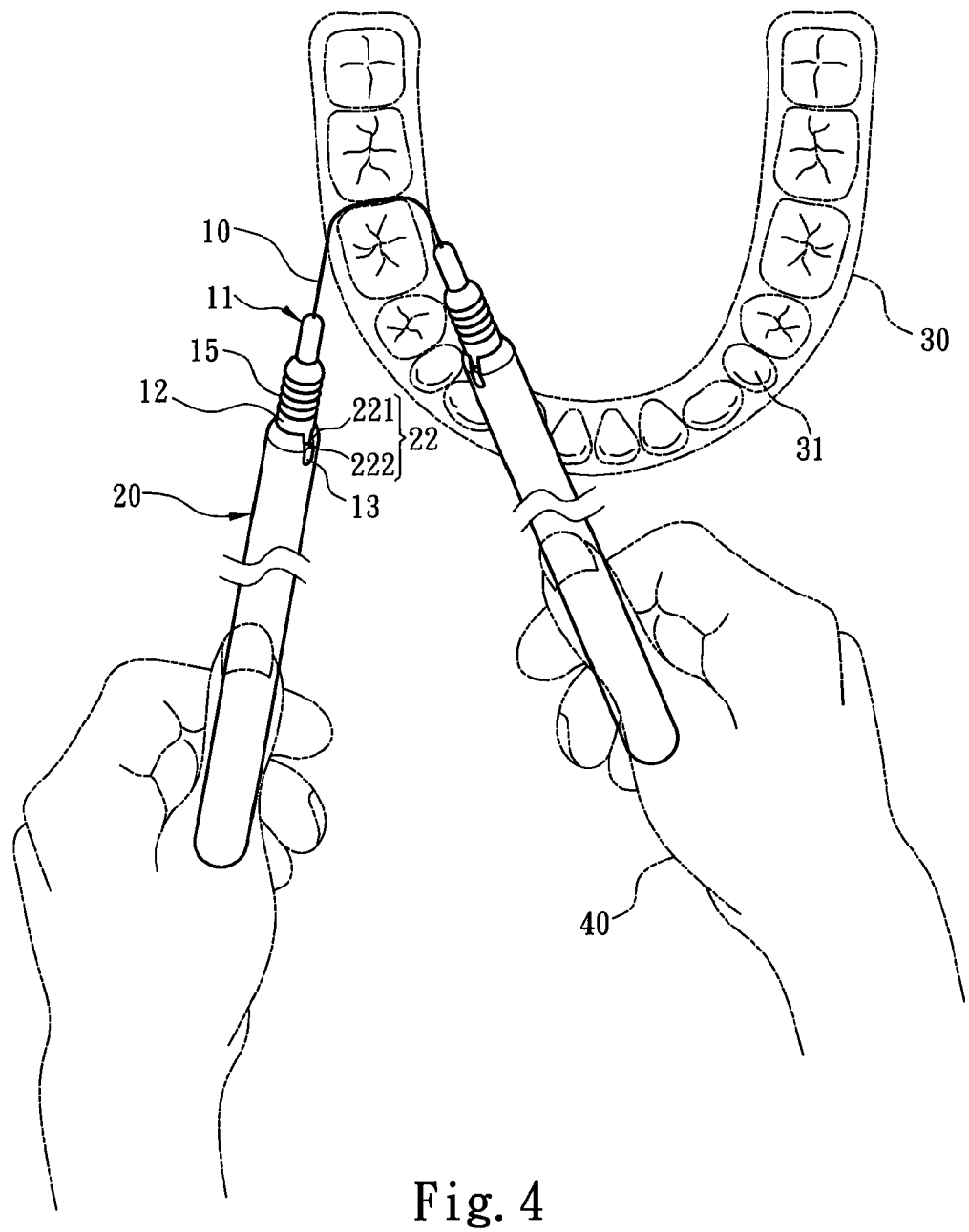
FIG. 4 is a schematic view showing the operation of the present invention.

Please refer to FIG. 4 which shows the application of the present invention. As operation, the two hands' fingers 40 respectively hold one holding body 20 and insert the two holding bodies 20 into the mouth 30, for employing the dental floss 10 mounted between the two holding bodies 20 to clean the slits between the teeth 31. Then, through operating, the user's fingers 40 are outside the mouth 30, and the teeth slits can be cleaned easily. Therefore, the bacteria or dirt on the fingers 40 will not be transferred into the mouth 30, thereby keeping the mouth 30 clean and hygiene.

In the aforesaid, the dental floss holding structure of the present invention includes a dental floss 10 and two holding bodies 20, wherein the two ends of the dental floss 10 are respectively connected with a base 11, and the base 11 and the holding body 20 respectively have a first coupling portion 12 and a second coupling portion 21. Furthermore, the first coupling portion 12 and the second coupling portion 21 respectively have a first positioning portion 13 and a second positioning portion 22, which are corresponding to each other, so that the dental floss 10 and the holding body 20 can have a stable fixed relationship therebetween through the engagement between the first and the second positioning portions 13, 22. Therefore, according to the above description, the present invention is advantageous that:

1. As operating, by using the holding bodies 20, the user's fingers 40 can be kept out of the mouth 30, thereby avoiding the entrance of the dirt or bacteria into the mouth 30, and thus achieving the hygiene of the mouth 30.

2. The diameter of the holding body 20 is relatively smaller than that of the fingers 40, so that the operation space in the mouth 30 is relatively larger, which provides more convenient and simpler operation procedure.

3. After using, the dental floss 10 together with the bases 11 can be detached from the holding bodies 20, so that not only the second coupling portions 21 of the holding bodies 20 can be cleaned for further assuring the hygiene of the mouth 30, but also the holding bodies 20 can be reused to achieve environmental protection.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A dental floss holding structure, comprising:
   a dental floss, whose two ends are respectively connected with a base, and each base including a first coupling portion with a first positioning portion mounted thereon; and
   two holding bodies, each of which includes a second coupling portion corresponding to the first coupling portion, and the second coupling portion including a second positioning portion corresponding to the first positioning portion, so that the dental floss and the holding bodies are stably fixed with each other through the engagement between the first and the second positioning portions;
   wherein the first positioning portion and the second positioning portion are respectively a protrusion and an indentation for receiving the protrusion; and
   wherein the indentation of the second positioning portion includes an inner wall which includes a locking block protruded therefrom to block the protrusion of the first positioning portion.

2. The dental floss holding structure as claimed in claim 1, wherein the first coupling portion is a column and the second coupling portion is a notch for receiving the column.

3. The dental floss holding structure as claimed in claim 1, wherein the first coupling portion and the second coupling portion further respectively include a first position-limiting portion and a second position-limiting portion.

4. The dental floss holding structure as claimed in claim 3, wherein the first position-limiting portion and the second position-limiting portion are respectively an indentation and a bulge for engaging with the indentation.

5. The dental floss holding structure as claimed in claim 1, wherein the base is provided with rough lines mounted on the surface thereof.

* * * * *